(12) United States Patent
Watanabe et al.

(10) Patent No.: US 10,352,849 B2
(45) Date of Patent: Jul. 16, 2019

(54) TERAHERTZ TIME DOMAIN SPECTROSCOPIC APPARATUS

(71) Applicant: FEMTO Deployments Inc., Okayama-shi, Okayama (JP)

(72) Inventors: Akira Watanabe, Okayama (JP); Tadashi Okuno, Okayama (JP); Takeji Ueda, Okayama (JP)

(73) Assignee: FEMTO DEPLOYMENTS INC., Okayama (JP)

( * ) Notice: Subject to any disclaimer, the term of this patent is extended or adjusted under 35 U.S.C. 154(b) by 0 days.

(21) Appl. No.: 16/094,133

(22) PCT Filed: Jul. 21, 2017

(86) PCT No.: PCT/JP2017/026456
§ 371 (c)(1),
(2) Date: Oct. 16, 2018

(87) PCT Pub. No.: WO2018/042938
PCT Pub. Date: Mar. 8, 2018

(65) Prior Publication Data
US 2019/0120757 A1    Apr. 25, 2019

(30) Foreign Application Priority Data
Aug. 31, 2016 (JP) ................... 2016-168869

(51) Int. Cl.
*G01N 21/35* (2014.01)
*G01N 21/3586* (2014.01)
*G01N 21/3577* (2014.01)

(52) U.S. Cl.
CPC ..... *G01N 21/3586* (2013.01); *G01N 21/3577* (2013.01)

(58) Field of Classification Search
CPC ........... G01N 21/3586; G01N 21/3577; G01N 21/3581; G01J 3/42
See application file for complete search history.

(56) References Cited

U.S. PATENT DOCUMENTS

| 2004/0065832 A1* | 4/2004 | Cluff .................. G01N 21/3581 250/341.1 |
| 2006/0197021 A1 | 9/2006 | Ouchi |

(Continued)

FOREIGN PATENT DOCUMENTS

| JP | 2006-064691 A | 3/2006 |
| JP | 2008-083020 A | 4/2008 |

(Continued)

OTHER PUBLICATIONS

Wang et al., Ulrabroadband THz Time-Domain Spectroscopy of a Free-Flowing Water Film; IEEE Transactions on Tetrahertz Science and Technology, vol. 4, No. 4, 425-431, Jul. 2014.

*Primary Examiner* — Marcus H Taningco
(74) *Attorney, Agent, or Firm* — Polsinelli PC (57) ABSTRACT

A terahertz wave is spectrally dispersed into two waves which are caused to pass through a sample liquid film 101 and a reference liquid film 102 and are then collected, and the terahertz waves in an interference state are detected by a terahertz wave detecting semiconductor 15. Consequently, only spectroscopic information related to a distinctive characteristic of the sample liquid film 101 is detected. In addition, a predetermined optical path length difference is provided between a path where the terahertz wave is transmitted through the sample liquid film 101 and a path where the terahertz wave is transmitted through the reference liquid film 102 by an optical delaying unit 17. Ina frequency spectrum obtained by performing Fourier transformation over a terahertz wave signal having an interference waveform by a terahertz wave signal analyzing device 20, con- (Continued)

sequently, a feature caused by an interaction of dissimilar molecules in the sample liquid film 101 appears in a spectral intensity at a frequency depending on the optical path length difference.

4 Claims, 5 Drawing Sheets

(56) References Cited

U.S. PATENT DOCUMENTS

| | | | |
|---|---|---|---|
| 2007/0229094 A1 | 10/2007 | Kasai et al. | |
| 2008/0006767 A1* | 1/2008 | Taday | G01S 13/887 250/252.1 |
| 2009/0225312 A1* | 9/2009 | Formanek | G01J 3/02 356/326 |
| 2009/0225313 A1* | 9/2009 | Umetsu | G01J 3/02 356/326 |
| 2009/0303480 A1* | 12/2009 | Tamada | G01J 3/02 356/369 |
| 2012/0305774 A1 | 12/2012 | Kiwa et al. | |
| 2014/0127707 A1* | 5/2014 | Ouchi | G01N 21/3586 435/7.1 |
| 2014/0146306 A1 | 5/2014 | Kubota | |
| 2016/0245703 A1 | 8/2016 | Takase et al. | |

FOREIGN PATENT DOCUMENTS

| | | |
|---|---|---|
| JP | 2011-127950 A | 6/2011 |
| JP | 2014-122875 A | 7/2014 |
| JP | 2015-219088 A | 12/2015 |
| JP | 2016-151562 A | 8/2016 |
| JP | 2017-078599 A | 4/2017 |
| WO | WO-2011/096563 A1 | 8/2011 |
| WO | WO 2012/165052 A1 | 12/2012 |

* cited by examiner

TERAHERTZ TIME DOMAIN SPECTROSCOPIC APPARATUS

CROSS REFERENCE TO RELATED APPLICATIONS

This application is a National Phase filing under 35 U.S.C. § 371 of PCT/JP2017/026456 filed on Jul. 21, 2017; and this application claims priority to Application No. 2016-168869 filed in Japan on Aug. 31, 2016. The entire contents of each application are hereby incorporated by reference.

TECHNICAL FIELD

The present invention relates to a terahertz time domain spectroscopic apparatus, and more particularly, is suitably used for a device having a sample arranged in a path through which a terahertz wave propagates, and serving to perform time domain measurement over a characteristic of the terahertz wave passing through the sample.

BACKGROUND ART

Conventionally, there is provided a spectroscopic device for measuring a characteristic of a substance by using an electromagnetic wave such as ultraviolet light, infrared light, a microwave, a terahertz wave or the like. Spectroscopy is classified into some methods depending on a physical amount to be measured by an electromagnetic wave. The methods include absorption spectroscopy and reflection spectroscopy. The absorption spectroscopy serves to transmit an electromagnetic wave through a sample to be a spectroscopic measurement target and to measure a physical property or a chemical property of the sample depending on a change in the electromagnetic wave which is caused by an intersection of the electromagnetic wave and the sample during passage through the sample. Moreover, the reflection spectroscopy is utilized for spectroscopic measurement of a material which does not transmit light therethrough, a material which scatters light or the like, and measures the property of the sample by analyzing light reflected from a sample surface.

Light is absorbed by a substance when energy of photon and an energy structure of a substance coincide with each other. For this reason, it is necessary to select a different light source or measurement technique in accordance with a phenomenon or structure to be observed in a sample serving as a measurement target. In general, an electromagnetic wave having a short wavelength (for example, ultraviolet light, infrared light, visible light or the like) is suitable for capturing a small structure or a strong interaction and an electromagnetic wave having a long wavelength (a terahertz wave or the like) is suitable for capturing a large structure or a weak interaction. Terahertz time domain spectroscopy (THz-TDS) serves to perform Fourier transformation over a time waveform of an electromagnetic wave obtained by directly measuring a waveform of a terahertz wave, thereby acquiring information about an amplitude and a phase of the terahertz wave.

A substance to be measured which is used as a spectroscopic measurement sample has gaseous, solid-like and liquid-like configurations and the like. Depending on the respective configurations, there is devised a method of arranging a substance to be measured in such a manner that an electromagnetic wave is transmitted properly. In order to perform measurement with high precision over a liquid-like sample, for example, a sample to be arranged in the spectroscopic apparatus is required to be formed so thinly that an electromagnetic wave is transmitted. In the case in which a liquid sample is subjected to spectroscopic measurement with a terahertz wave, particularly, it is necessary to perform the measurement by making a liquid into a plate-shaped uniform thin film and transmitting a terahertz wave through the plate-shaped part in order to prevent a reduction in an SN ratio of a measurement signal because of a great absorption effect of the terahertz wave through a water molecule.

In the measurement for a liquid sample, generally, the sample is inserted into a vessel (generally referred to as a solution cell) formed by a material for transmitting an electromagnetic wave, for example, glass and the electromagnetic wave is incident from an outside of the solution cell to measure the electromagnetic wave transmitted through the solution cell. When the liquid sample is inserted into the solution cell and is thus measured, however, spectroscopic information of a cell material is superposed as a noise on spectroscopic information of the liquid sample so that measurement of true spectroscopic information is disturbed.

In consideration of such a problem, conventionally, there is proposed an apparatus which is intended for enabling measurement of spectroscopic information with small noises without using a solution cell (for example, see Patent Documents 1 and 2). The apparatuses described in the Patent Documents 1 and 2 serve to use of a nozzle for directly causing the liquid sample to be thin-film shaped, and serve to jet a liquid sample from the nozzle by pressure of a pump, thereby generating a thin and flat plate-shaped liquid film.

Patent Document 1: Japanese Laid-Open Patent Publication No. 2011-127950

Patent Document 2: Japanese Laid-Open Patent Publication No. 2015-219088

DISCLOSURE OF THE INVENTION

An absorption spectrum of an organic molecule to be observed by the absorption spectroscopy described above has a peculiar spectrum structure to a molecule. Referring to the absorption spectroscopy using a terahertz wave, particularly, an intermolecular vibration is observed due to hydrogen bond or the like. However, an intermolecular interaction occurring in a sample in response to the terahertz wave has a complicated process and spectra tend to superimpose with each other, resulting in poor clear features. For this reason, there is a problem in that it is hard to know where the feature of the sample appears in a terahertz spectrum and the feature is very hard to find.

The present invention has been made to solve the problem and has an object to cause a feature depending on a characteristic of a sample to easily appear in a spectrum to be measured by terahertz time domain spectroscopy.

In order to solve the problem, the present invention spectrally disperses a terahertz wave generated from a terahertz light source into two waves and causes one of the terahertz waves to pass through a sample and the other terahertz wave to pass through a reference material, and focuses and detects the respective terahertz waves passing through the sample and the reference material, and performs Fourier transformation over a terahertz wave signal which is detected, thereby obtaining a frequency spectrum. In the present invention, moreover, an optical delaying unit for setting a delay quantity of a terahertz wave is provided in at least one of a path through which one of the terahertz waves propagates and a path through which the other terahertz wave propagates, and a predetermined difference is provided between the two paths.

According to the present invention having the structure described above, the terahertz wave passing through the sample and the terahertz wave passing through the reference material are detected in an interference state. If the sample and the reference material are made of the same substance, therefore, spectroscopic information of the sample is offset by that of the reference material. On the other hand, if the sample has a different characteristic from that of the reference material, spectroscopic information other than the different characteristic are offset so that only spectroscopic information related to the different characteristic, that is, a distinctive characteristic of the sample is detected.

When an optical path length difference is provided between a path where one of the terahertz waves propagates through the sample and a path where the other terahertz wave propagates through the reference material, particularly, a spectral intensity at a corresponding frequency to the optical path length difference appears as a deep recess in a frequency spectrum obtained by performing the Fourier transformation over a terahertz wave signal having an interference waveform. Then, a feature depending on the characteristic of the sample appears clearly in the spectral intensity portion appearing as the deep recess. Accordingly, it is possible to easily grasp the characteristic of the sample by analyzing the spectral intensity in the deep recess portion.

BEST MODE FOR CARRYING OUT THE INVENTION

Figure 1:
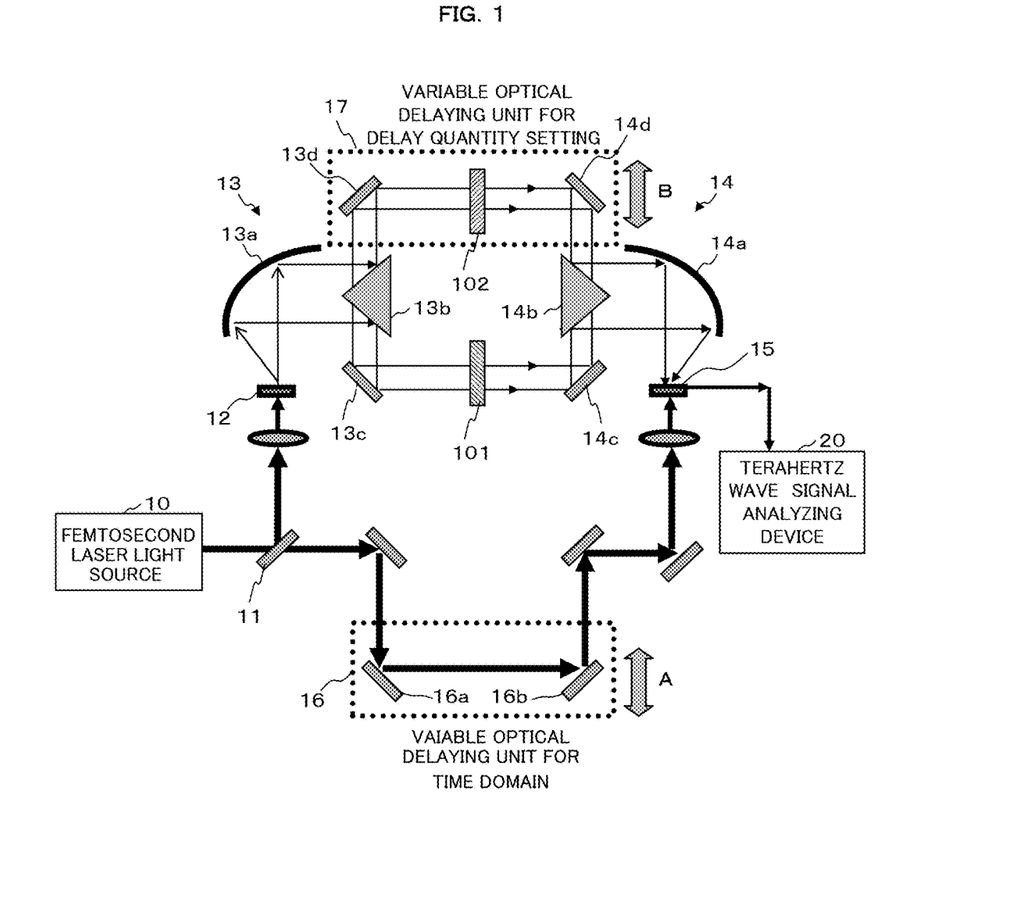
FIG. 1 is a view showing an example of a structure of a terahertz time domain spectroscopic apparatus according to the present embodiment.

An embodiment of the present invention will be described below with reference to the drawings. FIG. 1 is a view showing an example of a structure of a terahertz time domain spectroscopic apparatus according to the present embodiment. The terahertz time domain spectroscopic apparatus according to the present embodiment serves to arrange a liquid sample in a path through which a terahertz wave propagates and to perform time domain measurement over a characteristic of the terahertz wave transmitted through the liquid sample. More specifically, a time waveform of the terahertz wave transmitted through the liquid sample is detected and a detection signal is subjected to Fourier transformation to obtain a terahertz spectrum, thereby analyzing a characteristic of a liquid based on the spectrum.

As shown in FIG. 1, the terahertz time domain spectroscopic apparatus according to the present embodiment includes a femtosecond laser light source 10, a laser light spectral dispersing unit 11, a terahertz wave generating semiconductor 12 (corresponding to a terahertz light source in claims), a terahertz wave spectral dispersing unit 13, a terahertz wave focusing unit 14, a terahertz wave detecting semiconductor 15 (corresponding to a terahertz wave detecting unit in claims), a variable optical delaying unit 16 for time domain spectroscopy, a variable optical delaying unit 17 for delay quantity setting (corresponding to an optical delaying unit in claims), and a terahertz wave signal analyzing device 20 (corresponding to a terahertz wave signal analyzing unit in claims).

The laser light spectral dispersing unit 11 disperses laser light (a femtosecond laser pulse to be excitation light) to be emitted from the femtosecond laser light source 10 into two waves including pump light for operating the terahertz wave generating semiconductor 12 serving as a terahertz light source and sampling light for increasing weak current to be created by a terahertz wave which is incident on the terahertz wave detecting semiconductor 15 serving as a terahertz wave detecting unit. Specifically, the laser light spectral dispersing unit 11 is configured from a semitransparent mirror (half mirror).

The terahertz wave generating semiconductor 12 generates a terahertz wave in a predetermined frequency band by using laser light output from the laser light spectral dispersing unit 11. The terahertz wave spectral dispersing unit 13 spectrally disperses a terahertz wave to be generated from the terahertz wave generating semiconductor 12 into two waves. Specifically, the terahertz wave spectral dispersing unit 13 is configured from a first parabolic mirror 13a, a first triangular prism 13b, and two first reflection mirrors 13c and 13d.

The terahertz wave generated from the terahertz wave generating semiconductor 12 is reflected by the first parabolic mirror 13a and is output as a parallel bundle of rays. A terahertz wave to be the bundle of rays is reflected by two planes of the first triangular prism 13b respectively and is spectrally dispersed into two directions. The terahertz wave dispersed spectrally into one of the directions is reflected by the first reflection mirror 13c and is transmitted through a sample liquid film 101. The terahertz wave dispersed spectrally into the other direction is reflected by the first reflection mirror 13d and is transmitted through a reference liquid film 102. The sample liquid film 101 and the reference liquid film 102 will be described below in detail.

The terahertz wave focusing unit 14 focuses the terahertz wave transmitted through the sample liquid film 101 and the terahertz wave transmitted through the reference liquid film 102. Specifically, the terahertz wave focusing unit 14 is configured from a second parabolic mirror 14a, a second triangular prism 14b and two second reflection mirrors 14c and 14d.

One of the terahertz waves which is transmitted through the sample liquid film 101 is sequentially reflected by the second reflection mirror 14c and the second triangular prism 14b, and is then incident on the second parabolic mirror 14a. On the other hand, the other terahertz wave transmitted through the reference liquid film 102 is sequentially reflected by the second reflection mirror 14d and the second triangular prism 14b and is then incident on the second parabolic mirror 14a.

In other words, the second triangular prism 14b reflects one of the terahertz waves transmitted through the sample liquid film 101 and the other terahertz wave transmitted through the reference liquid film 102 by two planes into a single direction respectively and emits a bundle of rays of the terahertz wave transmitted through the sample liquid film 101 and the terahertz wave transmitted through the reference liquid film 102 toward the second parabolic mirror 14a.

The second parabolic mirror 14a reflects a bundle of rays incident in parallel from the second triangular prism 14b (a bundle of the terahertz waves transmitted through the sample liquid film 101 and the terahertz wave transmitted through the reference liquid film 102) and collects them into a focal point of the terahertz wave detecting semiconductor 15.

The terahertz wave detecting semiconductor 15 detects the terahertz wave focused by the terahertz wave focusing unit 14 and outputs a terahertz wave signal representing a waveform thereof. The terahertz wave signal analyzing device 20 performs Fourier transformation over the terahertz wave signal, thereby obtaining a frequency spectrum. By analyzing the frequency spectrum, it is possible to grasp the characteristic of the sample liquid film 101. In the present embodiment, particularly, the characteristic of the sample liquid film 101 is devised to easily appear in the frequency spectrum. The devising point will be described below in detail.

The variable optical delaying unit 16 for a time domain is provided in a path through which sampling light to be either laser light obtained by the laser light spectral dispersing unit 11 is propagated and variably sets a delay quantity of the sampling light. The variable optical delaying unit 16 for a time domain has two reflection mirrors 16a and 16b, and the reflection mirrors 16a and 16b are configured so as to be physically movable in parallel in a direction of an arrow A. Consequently, a delay time of the sampling light is made variable. The variable optical delaying unit 16 for a time domain is used for measuring a time variation in a terahertz wave while shifting a timing in which the sampling light reaches the terahertz wave detecting unit 15.

The variable optical delaying unit 17 for delay quantity setting is provided on a path through which either of two terahertz waves that is obtained by the terahertz wave spectral dispersing unit 13 and is transmitted through the reference liquid film 102 is propagated, and serves to variably set a delay quantity of the terahertz wave. The variable optical delaying unit 17 for delay quantity setting has the two reflection mirrors 13d and 14d and has a structure in which the reflection mirrors 13d and 14d are physically movable in parallel in a direction of an arrow B. The variable optical delaying unit 17 for delay quantity setting is used for making a predetermined difference between an optical length of a path where one of the terahertz waves transmitted through the sample liquid film 101 is propagated and an optical path length of a path where the other terahertz wave transmitted through the reference liquid film 102 is propagated.

Figure 2:
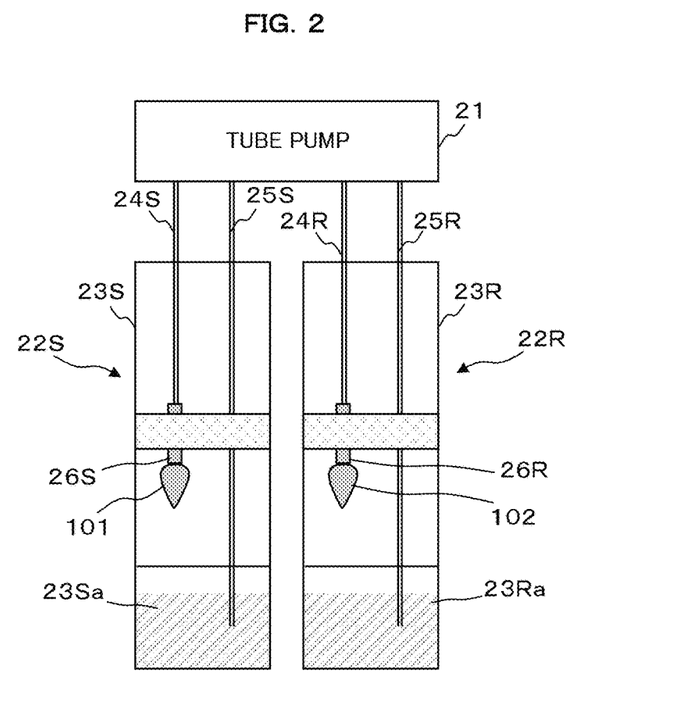
FIG. 2 is a view showing an example of a structure of a liquid circulating device for generating a liquid film according to the present embodiment.

FIG. 2 is a view showing an example of a structure of a liquid circulating device for generating the sample liquid film 101 and the reference liquid film 102. As shown in FIG. 2, the liquid circulating device according to the present embodiment includes a tube pump 21, a sample liquid film generating unit 22S for generating the sample liquid film 101 by using a measuring target liquid, and a reference liquid film generating unit 22R for generating the reference liquid film 102 by using a liquid for a reference.

The sample liquid film generating unit 22S includes a vessel 23S, an outgoing pipe 24S, a returning pipe 25S and a nozzle 26S. The vessel 23S is provided with a liquid tank 23Sa. Similarly, the reference liquid film generating unit 22R includes a vessel 23R, an outgoing pipe 24R, a returning pipe 25R and a nozzle 26R. The vessel 23R is provided with a liquid tank 23Ra. Thus, the sample liquid film generating unit 22S and the reference liquid film generating unit 22R have completely the same structures and are the same on a structure and mechanism basis.

The tube pump 21 sucks up a measuring target liquid through the returning pipe 25S from the liquid tank 23Sa of the sample liquid film generating unit 22S and derives the liquid sucked up to the nozzle 26S through the outgoing pipe 24S. The liquid is then jetted from the nozzle 26S so that the sample liquid film 101 is formed. The sample liquid film 101 is changed into a water droplet, and the water droplet is stored in the liquid tank 23Sa and is sucked up again by the tube pump 21.

Moreover, the tube pump 21 sucks up a liquid for a reference from the liquid tank 23Ra of the reference liquid film generating unit 22R through the returning pipe 25R and derives the liquid sucked up to the nozzle 26R through the outgoing pipe 24R. Then, the liquid is jetted from the nozzle 26R so that the reference liquid film 102 is formed. The reference liquid film 102 is changed into a water droplet, and the water droplet is stored in the liquid tank 23Ra and is sucked up again by the tube pump 21.

Thus, the liquid in the liquid tank 23Sa is circulated in the sample liquid film generating unit 22S and the sample liquid film 101 is formed by the nozzle 26S in the circulation process. Moreover, the liquid in the liquid tank 23Ra is circulated in the sample liquid film generating unit 22R and the reference liquid film 102 is formed by the nozzle 26R in the circulation process.

Herein, two liquids having different properties are stored in the liquid tank 23Sa of the sample liquid film generating unit 22S and the liquid tank 23Ra of the reference liquid film generating unit 22R, and are sucked up by the single tube pump 21 and are thus circulated so that the sample liquid film 101 and the reference liquid film 102 are formed. Then, the terahertz waves transmitted through the sample liquid film 101 and the reference liquid film 102 are detected by the terahertz wave detecting semiconductor 15 and a terahertz wave signal to be output from the terahertz wave detecting semiconductor 15 is analyzed by the terahertz wave signal analyzing device 20.

At this time, the variable optical delaying unit 17 for delay quantity setting which is added to an optical path of the terahertz wave on the reference liquid film 102 side is operated to vary a delay quantity of the terahertz wave on the reference liquid film 102 side, thereby performing regulation to make a predetermined optical path length difference between a path through which the terahertz wave on the sample liquid film 101 side propagates and a path through which the terahertz wave on the reference liquid film 102 side propagates.

According to the terahertz time domain spectroscopic apparatus in accordance with the present embodiment which is thus configured, the terahertz wave transmitted through the sample liquid film 101 and the terahertz wave transmitted through the reference liquid film 102 are simultaneously detected in an interference state by the terahertz wave detecting semiconductor 15. If the sample liquid film 101 and the reference liquid film 102 are formed of the same liquid, therefore, spectroscopic information of the sample liquid film 101 is offset by spectroscopic information of the reference liquid film 102. At this time, environments in the measurement of the terahertz wave, for example, a terahertz wave to be generated by the terahertz wave generating semiconductor 12, a temperature in the measurement, a pulsation to be generated on the liquid film by the operation of the tube pump 21 and the like are the same as in the sample liquid film 101 and the reference liquid film 102. Consequently, it is possible to enhance an offset effect.

In contrast, if the sample liquid film 101 has a different characteristic from that of the reference liquid film 102, spectroscopic information other than the different characteristic are offset so that only spectroscopic information related to the different characteristic, that is, a distinctive characteristic of the sample liquid film 101 is detected. Thus, the spectroscopic information related to the characteristic which is common to the sample liquid film 101 and the reference liquid film 102 are offset. Therefore, it is possible to sensitively detect the spectroscopic information related to the distinctive characteristic of the sample liquid film 101.

In the present embodiment, moreover, a predetermined optical path length difference is provided between the path where one of the terahertz waves transmitted through the sample liquid film 101 propagates and the path where the other terahertz wave transmitted through the reference liquid film 102 propagates. Consequently, a spectral intensity at a corresponding frequency to the optical path length difference appears as a deep recess in a frequency spectrum obtained by performing Fourier transformation over a terahertz wave signal having an interference waveform by the terahertz wave signal analyzing device 20. Then, a feature depending on an intermolecular interaction which is peculiar to the sample liquid film 101 appears clearly in a portion of the spectral intensity appearing as the deep recess. By analyzing the spectral intensity in the recess portion, accordingly, it is possible to easily grasp the characteristic of the sample liquid film 101.

For example, by storing beverage products just after production in the liquid tank 23Ra of the reference liquid film generating unit 22R and storing beverage products returned to the liquid tank 23Sa of the sample liquid film generating unit 22S to perform terahertz time domain spectroscopic measurement, it is possible to detect spectroscopic information representing a peculiar characteristic to the returned beverage products. For example, if some dissimilar molecules mix into the returned beverage product, it is possible to sensitively detect, as a terahertz wave signal, the spectroscopic information derived from the dissimilar molecules. When the terahertz wave signal is subjected to the Fourier transformation to obtain a frequency spectrum, a feature representing that the returned beverage product has a different characteristic from the beverage product just after production (a feature caused by an interaction of the dissimilar molecules) appears clearly in a portion having a deep recessed spectral intensity at a corresponding frequency to an optical path length difference between two paths. For this reason, it is possible to easily grasp whether the sample liquid film 101 includes dissimilar molecules which are not present in the reference liquid film 102.

Figure 3:
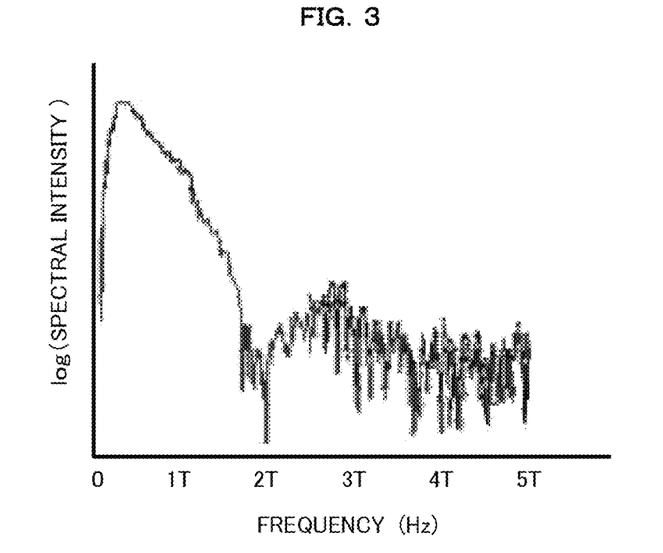
FIG. 3 is a chart showing an example of a frequency spectrum to be generated by the terahertz time domain spectroscopic apparatus according to the present embodiment.

FIG. 3 is a chart showing an example of a frequency spectrum which is obtained as a result of generation of the sample liquid film 101 and the reference liquid film 102 with the use of different liquids and execution of the Fourier transformation over the terahertz wave signal detected by the terahertz wave detecting semiconductor 15. An axis of ordinate in FIG. 3 has a logarithmic notation. A frequency spectrum shown in FIG. 3 is measured by using, as a liquid for a sample, a mixture of water and ethanol in a volume ratio of 40% after passage of approximately 20 minutes since the mixing (in the middle of the mixing) and using, as a liquid for a reference, the mixture after passage of approximately 70 minutes since the mixing (the mixing is completed). Moreover, the optical path length difference between the path where the terahertz wave is transmitted through the sample liquid film 101 and the path where the terahertz wave is transmitted through the reference liquid film 102 is set to be 250 fs (femtoseconds).

As shown in FIG. 3, a deep recess is generated on the spectral intensity in the vicinity of a frequency of 2 THz. The frequency of 2 THz is specified based on a relationship of an interference frequency=1/(2×optical path length difference). If a liquid for a sample and a liquid for a reference are equivalent to each other, the spectral intensity is zero at the frequency of 2 THz. In contrast, if the liquid for a sample and the reference for a reference are different from each other, a spectral intensity is not zero but has a finite value at the frequency of 2 THz as shown in FIG. 3. Accordingly, it is possible to easily grasp whether a dissimilar molecule which is not present in the liquid for a reference is mixed into the liquid for a sample or not by analyzing whether the spectral intensity is zero or not at a frequency where the spectral intensity is deeply recessed.

Even if the liquid for a sample and the liquid for a reference are equivalent to each other, the spectral intensity is not completely zero at the frequency where the spectral intensity is deeply recessed under the influence of a resolution of Fourier transformation, a fluctuation in air in measurement, a fluctuation in a temperature, a light noise or an electric noise in the measurement, or the like. Therefore, it is also possible to detect whether the dissimilar molecule which is not present in the liquid for a reference is mixed into the liquid for a sample by analyzing whether the spectral intensity is equal to or smaller than a predetermined threshold.

As described above in detail, in the present embodiment, the terahertz wave to be generated from the terahertz wave generating semiconductor 12 is spectrally dispersed into two waves by the terahertz wave spectral dispersing unit 13 to transmit one of the terahertz waves through the sample liquid film 101 and to transmit the other terahertz wave through the reference liquid film 102, thereby focusing the respective terahertz waves transmitted through the sample liquid film 101 and the reference liquid film 102 and detecting them by the terahertz wave detecting semiconductor 15.

According to the present embodiment having such a structure, the terahertz wave transmitted through the sample liquid film 101 and the terahertz wave transmitted through the reference liquid film 102 are simultaneously detected in an interference state. Therefore, it is possible to offset the spectroscopic information related to the characteristic possessed by the sample liquid film 101 and the reference liquid film 102 in common. For this reason, if the sample liquid film 101 has a different characteristic from that of the reference liquid film 102, spectroscopic information other than the different characteristic are offset so that only spectroscopic information related to the different characteristic, that is, the distinctive characteristic of the sample liquid film 101 is detected. According to the present embodiment, consequently, it is possible to detect the spectroscopic information of the liquid sample with high sensitivity.

According to the present embodiment, moreover, the predetermined optical path length difference is made between the path where the terahertz wave transmitted through the sample liquid film 101 propagates and the path where the terahertz wave transmitted through the reference liquid film 102 propagates. In a frequency spectrum obtained by performing the Fourier transformation over the terahertz wave signal of an interference waveform, therefore, a feature indicating that the dissimilar molecule which is not present in the reference liquid film 102 is contained in the sample liquid film 101 appears clearly in the portion of the spectral intensity appearing as the deep recess at the corresponding frequency to the optical path length difference. By analyzing the spectral intensity of the recess portion, accordingly, it is possible to easily grasp whether the sample liquid film 101 has a different characteristic from that of the reference liquid film 102 or not.

Figure 4:
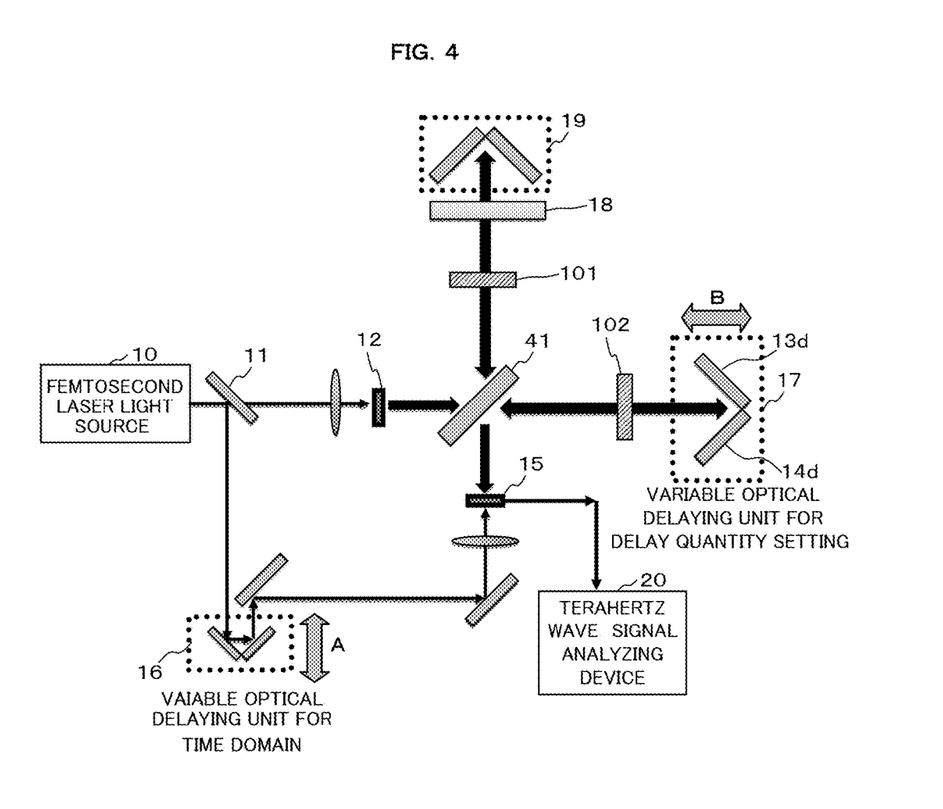
FIG. 4 is a view showing another example of the structure of the terahertz time domain spectroscopic apparatus according to the present embodiment.

FIG. 4 is a view showing an example of another structure of the terahertz time domain spectroscopic apparatus according to the present embodiment. Since components having the same reference numerals as those shown in FIG. 1 have the same functions in FIG. 4, repetitive description will be omitted herein. Referring to the terahertz time domain spectroscopic apparatus shown in FIG. 4, structures of a terahertz wave spectral dispersing unit and a terahertz wave focusing unit and paths where a terahertz wave is transmitted through a sample liquid film 101 and a reference liquid film 102 are different from those in the example of the structure in FIG. 1.

In other words, the terahertz time domain spectroscopic apparatus shown in FIG. 4 includes a semitransparent mirror (half mirror) 41 in place of the terahertz wave spectral dispersing unit 13 and the terahertz wave focusing unit 14 shown in FIG. 1. The half mirror 41 serves as the terahertz wave spectral dispersing unit and the terahertz wave focusing unit.

In other words, the half mirror 41 serving as the terahertz wave spectral dispersing unit spectrally disperses a terahertz wave generated from terahertz wave generating semiconductor 12 into two directions. More specifically, the half mirror 41 is provided at an angle of 45 degrees with respect to the terahertz wave generating semiconductor 12, and reflects a part of the terahertz wave generated from the terahertz wave generating semiconductor 12 at the angle of 45 degrees and transmits the part, thereby performing the spectral division into the direction of the sample liquid film 101 and that of the reference liquid film 102.

The terahertz wave transmitted through the sample liquid film 101 is reflected by a reflection mirror 19 via an attenuation filter 18 and follows an original path toward the half mirror 41. Moreover, the terahertz wave transmitted through the reference liquid film 102 is reflected by the reflection mirrors 13d and 14d possessed by the variable optical delaying unit 17 for delay quantity setting and follows the original path toward the half mirror 41.

The half mirror 41 serving as the terahertz wave focusing unit transmits one of the terahertz waves transmitted through the sample liquid film 101, and furthermore, reflects the other terahertz wave transmitted through the reference liquid film 102 at the angle of 45 degrees, thereby collecting the two terahertz waves in a direction of the terahertz wave detecting semiconductor 15.

Figure 5:
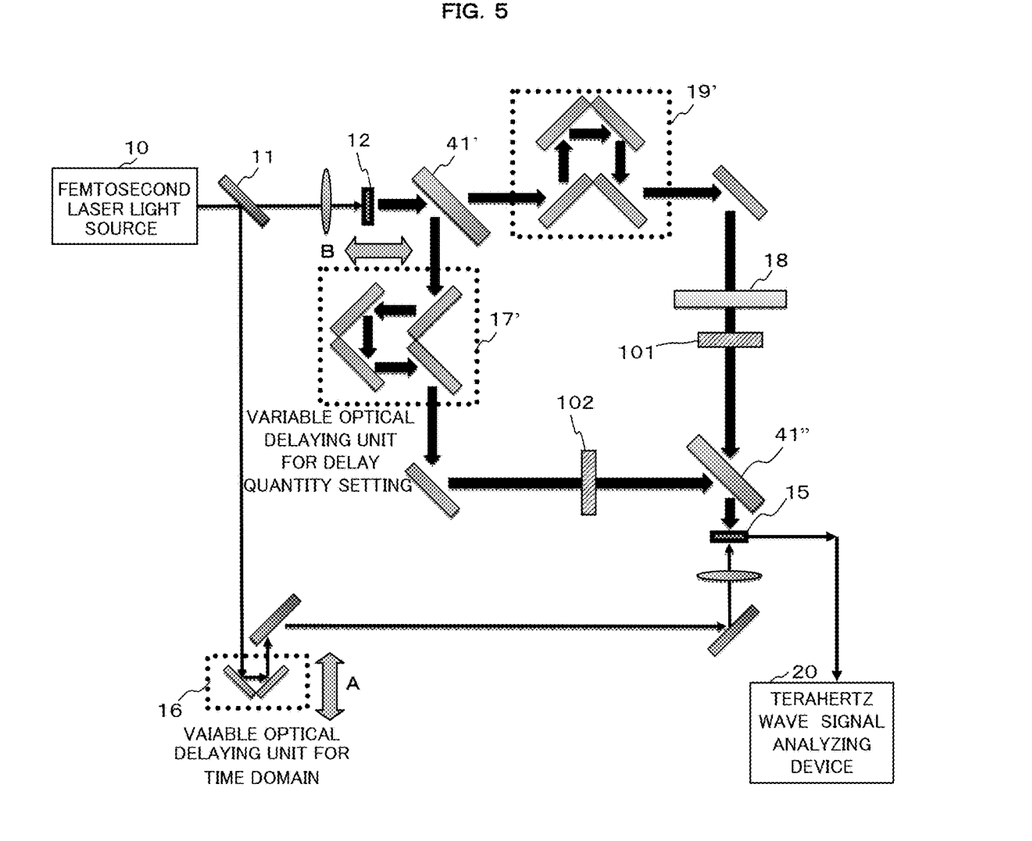
FIG. 5 is a view showing yet another example of the structure of the terahertz time domain spectroscopic apparatus according to the present embodiment.

FIG. 5 is a view showing yet another example of the structure of the terahertz time domain spectroscopic apparatus according to the present embodiment. Since components having the same reference numerals as those shown in FIG. 4 have the same functions in FIG. 5, repetitive description will be omitted herein.

In the terahertz time domain spectroscopic apparatus shown in FIG. 5, the function of the half mirror 41 shown in FIG. 4 is implemented by two half mirrors 41' and 41". In other words, the first half mirror 41' corresponds to the terahertz wave spectral dispersing unit and the second half mirror 41" corresponds to the terahertz wave focusing unit.

The first half mirror 41' spectrally disperses the terahertz wave generated from the terahertz wave generating semiconductor 12 into two directions. In other words, the first half mirror 41' is provided at an angle of 45 degrees with respect to the terahertz wave generating semiconductor 12 and reflects a part of the terahertz wave generated from the terahertz generating semiconductor 12 at the angle of 45 degrees, and furthermore, transmits the part therethrough to spectrally disperse the wave into the path on a side where the sample liquid film 101 is provided and the path on a side where the reference liquid film 102 is provided.

The second half mirror 41" is provided at the angle of 45 degrees with respect to the terahertz wave detecting semiconductor 15 and transmits one of the terahertz waves transmitted through the sample liquid film 101, and furthermore, reflects the other terahertz wave transmitted through the reference liquid film 102 at the angle of 45 degrees, thereby collecting the two terahertz waves in the direction of the terahertz wave detecting semiconductor 15.

Moreover, the terahertz time domain spectroscopic apparatus shown in FIG. 5 includes a variable optical delaying unit 17' for delay quantity setting and a reflection mirror 19' in place of the variable optical delaying unit 17 for delay quantity setting and the reflection mirror 19 shown in FIG. 4. The variable optical delaying unit 17' for delay quantity setting and the reflection mirror 19' use different numbers of reflection mirrors from each other and have substantially identical functions to the variable optical delaying unit 17 for delay quantity setting and the reflection mirror 19.

The terahertz wave transmitted through the first half mirror 41' is reflected by the reflection mirror 19' and is then transmitted through the sample liquid film 101 via the attenuation filter 18 toward the second half mirror 41". Moreover, the terahertz wave reflected at the angle of 45 degrees by the first half mirror 41' is reflected by a reflection mirror possessed by the variable optical delaying unit 17' for delay quantity setting and is then transmitted through the reference liquid film 102 toward the second half mirror 41".

As described above, the second half mirror 41" collects one of the terahertz waves transmitted through the sample liquid film 101 and the other terahertz wave transmitted through the reference liquid film 102 in the direction of the terahertz wave detecting semiconductor 15.

There is an advantage that the structure can be more simplified as compared with FIG. 1 by configuring the terahertz time domain spectroscopic apparatus as shown in FIG. 4 or FIG. 5. Although FIGS. 1, 4 and 5 are shown as examples of the structure of the terahertz time domain spectroscopic apparatus in the present embodiment, these are only illustrative and the present invention is not restricted to these structures.

Although the description has been given to the example in which the variable optical delaying unit 17 for delay quantity setting is provided on the optical path where the terahertz wave is transmitted through the reference liquid film 102 in the embodiment, the variable optical delaying unit 17 for delay quantity setting may be provided on the optical path at the sample liquid film 101 side. Alternatively, the variable optical delaying unit 17 for delay quantity setting may be provided on both the optical path at the sample liquid film 101 side and the optical path at the reference liquid film 102 side.

Although the description has been given to the example in which the delay quantity of the terahertz wave is regulated by the variable optical delaying unit 17 for delay quantity setting in the embodiment of FIG. 1, the apparatus may further include a liquid film moving unit for moving an arrangement position of the reference liquid film 102 in conformity with the movement of the reflection mirrors 13d and 14d possessed by the variable optical delaying unit 17 for delay quantity setting. For example, it is possible to configure the liquid film moving unit by forming the nozzle 26R so as to be movable physically in parallel in the direction of the arrow B. In the case in which the variable optical delaying unit 17 for delay quantity setting is provided on the optical path at the sample liquid film 101 side, the nozzle 26S is configured to be physically movable in parallel.

Although the description has been given to the example in which the sample liquid film 101 is provided between the reflection mirrors 13c and 14c and the reference liquid film 102 is provided between the reflection mirrors 13d and 14d in the first embodiment of FIG. 1, moreover, the present invention is not restricted thereto. For example, the sample liquid film 101 may be provided between the first triangular prism 13b and the first reflection mirror 13c and the reference liquid film 102 may be provided between the first triangular prism 13b and the first reflection mirror 13d. In this case, the terahertz wave spectral dispersing unit is configured from the first parabolic mirror 13a and the first triangular prism 13b.

While the description has been given to the example in which the variable optical delaying unit 16 for a time domain is provided in the path through which the sampling light propagates in the embodiment, moreover, the variable optical delaying unit 16 for a time domain may be provided in a path through which pump light propagates.

While the description has been given to the example in which the optical path length difference between the path where the terahertz wave is transmitted through the sample liquid film 101 and the path where the terahertz wave is transmitted through the reference liquid film 102 is set to be 250 fs in the embodiment, moreover, the numeric value is only illustrative and the present invention is not restricted thereto. While the description has been given to the structure for variably setting the delay quantity of the terahertz wave to be transmitted through the reference liquid film 102 by the variable optical delaying unit 17 for delay quantity setting in the embodiment, furthermore, the present invention is not restricted thereto. For example, the delay quantity of the terahertz wave may be fixedly set to a predetermined value.

Figure 6:
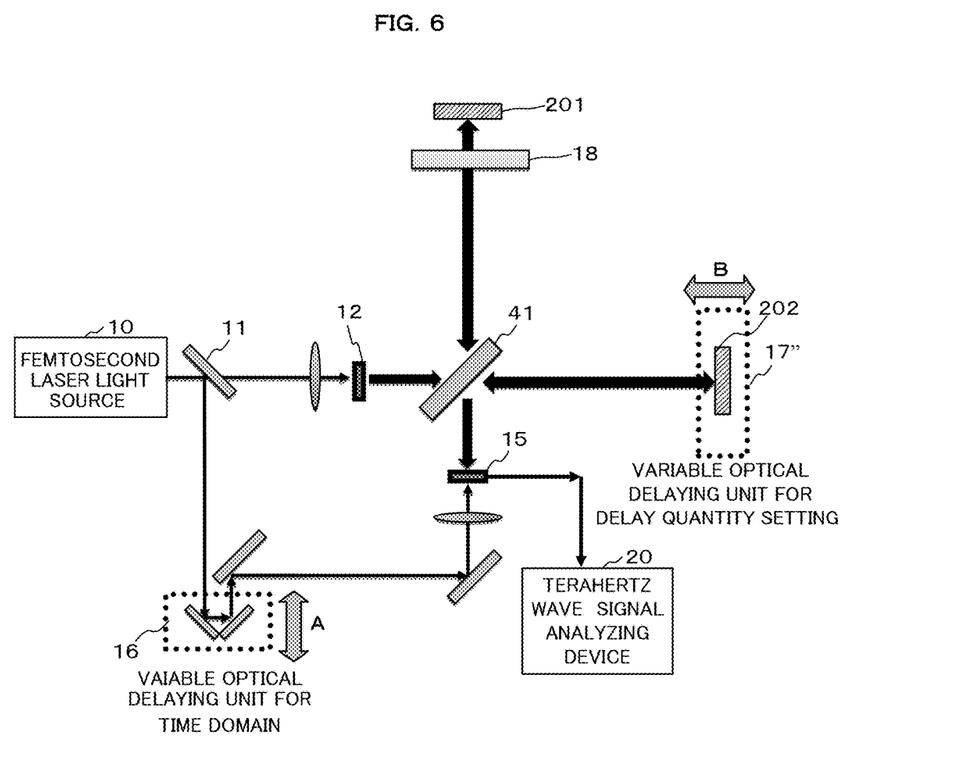
FIG. 6 is a view showing a further example of the structure of the terahertz time domain spectroscopic apparatus according to the present embodiment.

While the description has been given to the example in which the terahertz time domain spectroscopic apparatus according to the present invention is applied to the absorption spectroscopy, the apparatus can also be applied to reflection spectroscopy. FIG. 6 is a view showing an example of the structure of the terahertz time domain spectroscopic apparatus in the case of the application to the reflection spectroscopy. Since the components having the same reference numerals as those shown in FIG. 4 have the same functions in FIG. 6, repetitive description will be omitted herein.

With the structure shown in FIG. 6, a sample 201 and a reference material 202 are used in place of the sample liquid film 101 and the reference liquid film 102. The sample 201 and the reference material 202 are formed by materials which do not transmit light therethrough or materials which scatter light. Moreover, the apparatus includes a variable optical delaying unit 17" for delay quantity setting in place of the variable optical delaying unit 17 for delay quantity setting. The variable optical delaying unit 17" for delay quantity setting sets an optical delay quantity by moving an arrangement position of the reference material 202. The structure of the terahertz time domain spectroscopic apparatus related to the reflection spectroscopy is only illustrative in FIG. 6 and the present invention is not restricted thereto.

While the description has been given to the case in which the spectroscopic information about beverage products are measured as an example of the use of the terahertz time domain spectroscopic apparatus in the embodiment, furthermore, it is apparent that the apparatus can be used in the other cases. For example, two samples obtained by DNA proliferation in PCR (Polymerase Chain Reaction) to be performed in genetic study or the like are used as the sample liquid film 101 and the reference liquid film 102 which are caused to transmit terahertz waves therethrough to carry out Fourier transformation over terahertz wave signals having interference waveforms thus detected so that a frequency spectrum is acquired. Consequently, it is possible to easily grasp the presence of a difference between the characteristics of the two samples. Thus, it is possible to instantly detect a difference to be made by a PCR error and the apparatus can be used as an advantageous evaluating method.

Furthermore, the terahertz time domain spectroscopic apparatus according to the present embodiment can be utilized for a liquid substance to be measured which is used as a spectroscopic measurement sample. In a general environment, water or vapor is always present. At the same time, an effect for absorbing a terahertz wave by a water molecule is great. Therefore, the terahertz wave is absorbed by just a little water or vapor, which disturbs original measurement. In an environment in which many noises are made for the measurement of the terahertz wave, thus, the terahertz time domain spectroscopic apparatus according to the present embodiment is particularly effective.

In addition, the embodiment is only illustrative for concreteness to carry out the present invention and the technical scope of the present invention should not be thereby construed to be restrictive. In other words, the present invention can be carried out in various configurations without departing from the gist or main features thereof.

EXPLANATION OF DESIGNATION 11 laser light spectral dispersing unit
12 terahertz wave generating semiconductor (terahertz wave light source)
13 terahertz wave spectral dispersing unit
13a first parabolic mirror
13b first triangular prism
13c, 13d first reflection mirror
14 terahertz wave focusing unit
14a second parabolic mirror
14b second triangular prism
14c, 14d second reflection mirror
15 terahertz wave detecting semiconductor (terahertz wave detecting unit)
16 variable optical delaying unit for time domain
17, 17', 17" variable optical delaying unit for delay quantity setting (optical delaying unit)
20 terahertz wave signal analyzing device (terahertz wave signal analyzing unit)
41 half mirror (terahertz wave spectral dispersing unit and terahertz wave focusing unit)
41' half mirror (terahertz wave spectral dispersing unit)
41" half mirror (terahertz wave focusing unit)
101 sample liquid film
102 reference liquid film 201 sample
202 reference material

The invention claimed is:

1. A terahertz time domain spectroscopic apparatus for arranging a sample in a path through which a terahertz wave propagates and time domain measuring a characteristic of the terahertz wave passing through the sample, the apparatus comprising:
   a terahertz wave spectral dispersing unit for spectrally dispersing a terahertz wave generated from a terahertz light source into two waves;
   a terahertz wave focusing unit for focusing a terahertz wave passing through the sample arranged in a path where one of the terahertz waves dispersed spectrally by the terahertz wave spectral dispersing unit propagates and a terahertz wave passing through a reference material arranged in a path where the other terahertz wave dispersed spectrally by the terahertz wave spectral dispersing unit propagates;
   an optical delaying unit for setting a delay quantity of a terahertz wave in at least one of the path through which one of the terahertz waves propagates and the path through which the other terahertz wave propagates;
   a terahertz wave detecting unit for detecting the terahertz wave focused by the terahertz wave focusing unit and outputting a terahertz wave signal representing a waveform thereof; and
   a terahertz wave signal analyzing unit for performing Fourier transformation over the terahertz wave signal output from the terahertz wave detecting unit, thereby obtaining a frequency spectrum,
   wherein a predetermined difference is provided between an optical path length of the path through which one of the terahertz waves propagates and an optical path length of the path through which the other terahertz wave propagates by the optical delaying unit.

2. The terahertz time domain spectroscopic apparatus according to claim 1, wherein
   the terahertz wave spectral dispersing unit includes:
   a first parabolic mirror for reflecting a terahertz wave generated from the terahertz light source and outputting a parallel bundle of rays; and
   a first triangular prism for reflecting a terahertz wave serving as the bundle of rays to be propagated from the first parabolic mirror by two planes respectively and spectrally dispersing the reflected terahertz wave into two directions, and the terahertz wave focusing unit includes:
   a second triangular prism for reflecting one of the two terahertz waves dispersed spectrally by the first triangular prism which passes through the sample and the other terahertz wave of the two terahertz waves which passes through the reference material into a single direction by two planes respectively and emitting a bundle of rays of the terahertz wave passing through the sample and the terahertz wave passing through the reference material; and
   a second parabolic mirror for collecting the terahertz wave to be the bundle of rays which is incident in parallel from the second triangular prism onto a focal point of the terahertz wave detecting unit.

3. The terahertz time domain spectroscopic apparatus according to claim 1, wherein
   the terahertz wave spectral dispersing unit is configured from a half mirror for spectrally dispersing the terahertz wave generated from the terahertz light source into two directions, and
   the terahertz wave focusing unit is also configured from the half mirror,
   the terahertz wave focusing unit collects one of two terahertz waves dispersed spectrally by the half mirror which passes through the sample and the other terahertz wave of the two terahertz waves dispersed spectrally by the half mirror which passes through the reference material in a direction of the terahertz wave detecting unit.

4. The terahertz time domain spectroscopic apparatus according to claim 1, wherein
   the terahertz wave spectral dispersing unit is configured from a first half mirror for spectrally dispersing a terahertz wave generated from the terahertz light source into two directions, and
   the terahertz wave focusing unit is configured from s second half mirror for collecting one of two terahertz waves dispersed spectrally by the first half mirror which passes through the sample and the other terahertz wave of the two terahertz waves dispersed spectrally by the first half mirror which passes through the reference material in a direction of the terahertz wave detecting unit.

* * * * *